United States Patent
Chapman et al.

(10) Patent No.: US 7,272,441 B1
(45) Date of Patent: Sep. 18, 2007

(54) EXTERNAL DEFIBRILLATOR AND METHODS FOR OPERATING THE EXTERNAL DEFIBRILLATOR

(75) Inventors: Fred W. Chapman, Newcastle, WA (US); Robert G. Walker, Bothell, WA (US); Joseph L. Sullivan, Kirkland, WA (US)

(73) Assignee: Medtronic Physio-Control Manufacturing Corp., Redmond, WA (US)

( * ) Notice: Subject to any disclaimer, the term of this patent is extended or adjusted under 35 U.S.C. 154(b) by 203 days.

(21) Appl. No.: 10/712,469

(22) Filed: Nov. 12, 2003

Related U.S. Application Data

(60) Provisional application No. 60/426,123, filed on Nov. 13, 2002.

(51) Int. Cl.
*A61N 1/00* (2006.01)
(52) U.S. Cl. ............... 607/5; 607/3; 607/62; 607/63; 128/908
(58) Field of Classification Search ............... 607/3, 607/5, 6, 42, 62, 63, 142; 128/908
See application file for complete search history.

(56) References Cited

U.S. PATENT DOCUMENTS

| | | | |
|---|---|---|---|
| 5,222,480 A * | 6/1993 | Couche et al. ............ | 607/5 |
| 5,607,454 A | 3/1997 | Cameron et al. | |
| 6,029,085 A | 2/2000 | Olson et al. | |
| 6,356,785 B1 * | 3/2002 | Snyder et al. ............ | 607/5 |
| 6,553,257 B2 * | 4/2003 | Snyder et al. ............ | 607/5 |
| 6,556,865 B2 * | 4/2003 | Walcott et al. ............ | 607/6 |
| 6,807,442 B1 * | 10/2004 | Myklebust et al. ......... | 600/509 |
| 2002/0165585 A1 * | 11/2002 | Dupelle et al. ............ | 607/5 |

* cited by examiner

*Primary Examiner*—Robert E. Pezzuto
*Assistant Examiner*—Natasha Patel

(57) ABSTRACT

Methods and apparatus are provided for minimizing the inherent time delays within external defibrillators and allowing operators to administer CPR therapy as close in time as possible to the delivery of a defibrillation shock to a patient. The methods and apparatuses utilize timing schemes for initiation and completion of charging or maintaining the charge of an energy storage device of an external defibrillator for at least a portion of a predetermined CPR therapy delivery time.

18 Claims, 3 Drawing Sheets

EXTERNAL DEFIBRILLATOR AND METHODS FOR OPERATING THE EXTERNAL DEFIBRILLATOR

CROSS-REFERENCES TO RELATED APPLICATIONS

This application claims the benefit of U.S. Provisional Application No. 60/426,123, filed Nov. 13, 2002.

TECHNICAL FIELD

This invention generally relates to external defibrillators, and more particularly to an external defibrillator and methods of operating the external defibrillator that allow a user to deliver CPR therapy to a patient before the administration of a defibrillation shock.

BACKGROUND OF THE INVENTION

Defibrillators are devices for providing life-saving electrical shock therapy to persons experiencing an irregular heart beat, such as Ventricular Fibrillation (VF). A defibrillator provides an electrical shock to the heart, in order to convert the irregular heart beat to a normal sinus rhythm. One type of defibrillator is surgically implanted in patients who are considered likely to need electrical shock therapy, precluding the necessity of constant monitoring by medical personnel.

A more commonly used type of defibrillator is the external defibrillator, which sends electrical shock pulses to the patient's heart through external electrodes applied to the patient's chest. External defibrillators may be manually operated, as are typically used in hospitals by medical personnel or may be semi-automatic, semi-automated, fully automatic, or fully automated devices, where they can be used in any location where an unanticipated need may occur.

Recent research has shown that administration of CPR therapy close to the time of the delivery of a defibrillation shock may be beneficial to a patient. Prior art defibrillator configurations have attempted to apply this finding by compressing the time gap between the analysis of the patient's ECG signal and the delivery of the defibrillation shock. However, these attempts have presented problems. For instance, one known defibrillator includes circuitry that reduces the charging time of the energy storage device. These types of defibrillators include complex circuitry, which can add more components to the defibrillator and increase the overall size of the apparatus. In certain instances, increase in size may not be favorable, especially because users of external defibrillators typically may need to travel from one site to another to administer treatment. Thus, a large, bulky machine may not be desirable. Moreover, the additional circuitry may be more costly to implement, and thereby may increase the price of the defibrillator.

Other defibrillators begin to charge the energy storage device as soon as power is turned on. However, a decision to shock is generally rendered in less than fifty percent (50%) of all cardiac arrest cases, and charging the energy storage device at every power on instance may reduce battery life. Yet other defibrillators allow caregivers to administer CPR therapy during the collection and analysis of the patient's heart rhythm data. However, added outside physical movement of the patient may cause the defibrillator to collect inaccurate data.

Accordingly, it is desirable to find a solution that allows the delivery of CPR therapy before the administration of a defibrillator shock that does not compromise the safety of the user or patients, or increase the costs or size of the defibrillators. In addition, it is desirable to implement the solution in all types of external defibrillators, including fully automatic, semi-automatic, fully automated or semi-automated and manual defibrillators. Furthermore, other desirable features and characteristics of the invention will become apparent from the subsequent detailed description of the invention and the appended claims, taken in conjunction with the accompanying drawings and this background of the invention.

SUMMARY OF THE INVENTION

According to an exemplary embodiment of the invention, a method is provided that includes the steps of determining whether the patient has a heart rhythm treatable with a defibrillation shock, charging an energy storage device to a change magnitude during a predetermined CPR therapy period, and after the predetermined CPR therapy period, discharging the energy storage device to thereby supply the defibrillation shock to the patient.

In another exemplary embodiment of the invention, another method for controlling an external defibrillator is provided. The method includes determining whether the patient has a heart rhythm treatable with a defibrillation shock. The method also includes, for a predetermined CPR therapy period, charging an energy storage device to a charge magnitude and maintaining the charge magnitude. Lastly, the method includes, after the predetermined CPR therapy period, discharging the energy storage device to thereby supply the defibrillation shock to the patient.

In yet another exemplary embodiment of the invention, an external defibrillator is provided that includes, a plurality of electrodes, an energy storage device and a controller. The plurality of electrodes is configured to deliver a defibrillation shock to, and sense one or more physical parameters associated with, the patient. The energy storage device is coupled to the plurality of electrodes and configured to store a charge. The controller, coupled to the plurality of electrodes and the energy storage device, is configured to determine whether the patient has a heart rhythm treatable with a defibrillation shock, charge the energy storage device to a charge magnitude for a predetermined CPR therapy period and after the predetermined CPR therapy period, discharge the energy storage device to thereby supply the defibrillation shock to the patient.

In another embodiment of the invention, an external defibrillator is provided that includes, a plurality of electrodes, an energy storage device and a controller. Just as above, the plurality of electrodes is configured to deliver a defibrillation shock to, and sense one or more physical parameters associated with, the patient, the energy storage device is coupled to the plurality of electrodes and configured to store a charge, and the controller is coupled to the plurality of electrodes and the energy storage device. In this embodiment, the controller is configured to determine whether the patient has a heart rhythm treatable with a defibrillation shock, and for a predetermined CPR therapy period, charge the energy storage device to a predetermined charge magnitude and also maintain the charge, discharge the energy storage device to thereby supply the defibrillation shock to the patient.

In yet another embodiment, a method of controlling an external defibrillator configured to supply a defibrillation shock to a patient is provided. The method includes obtaining and analyzing a physical parameter of the patient to determine whether the patient should be treated with a defibrillation shock, prompting a user to deliver CPR therapy for a predetermined CPR therapy period based, in part, on the physical parameter, charging an energy storage device to a charge magnitude that is at least partially based on the physical parameter, for a predetermined charge time beginning at a time instant during the predetermined CPR therapy period, and discharging the energy storage device to thereby supply the defibrillation shock to the patient, after the predetermined CPR therapy period.

BRIEF DESCRIPTION OF THE DRAWINGS

The invention will hereinafter be described in conjunction with the following drawing figures, wherein like numerals denote like elements.

DETAILED DESCRIPTION OF EXEMPLARY EMBODIMENTS

The following detailed description of the invention is merely exemplary in nature and is not intended to limit the invention or the application and uses of the invention. Furthermore, there is no intention to be bound by any expressed or implied theory presented in the preceding background of the invention or the following detailed description of the invention.

Figure 1:
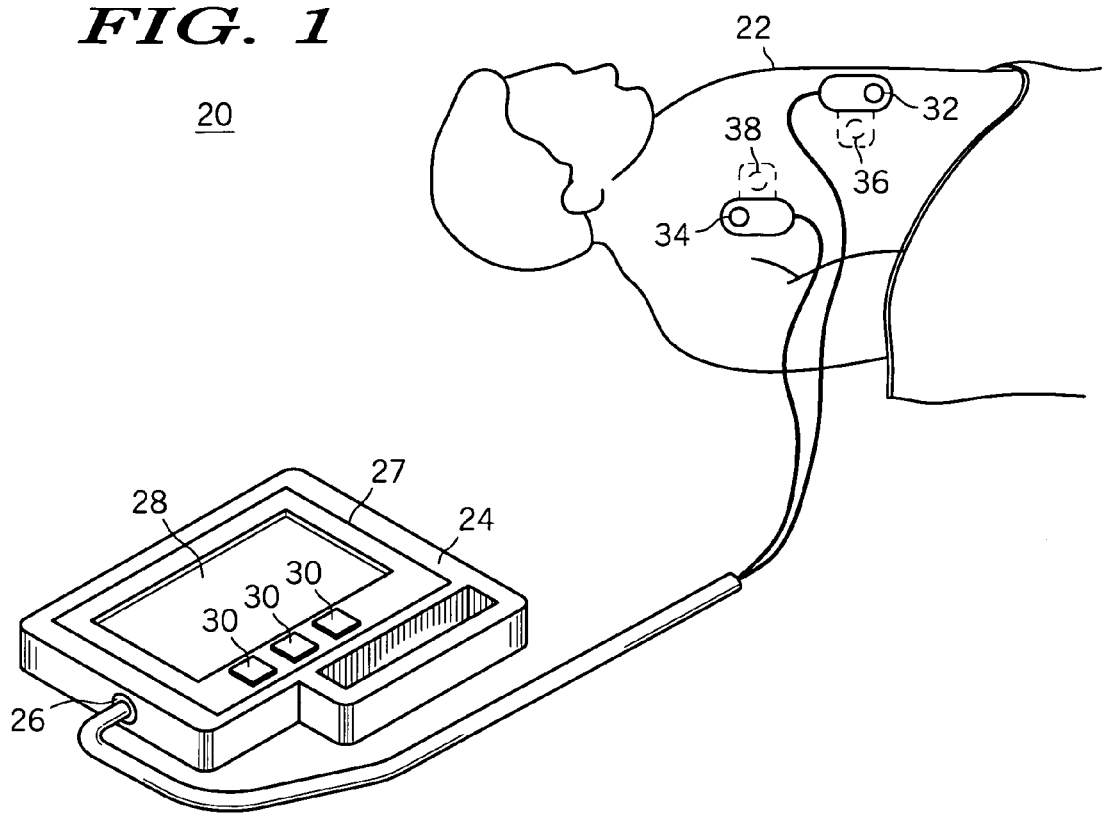
FIG. 1 is an illustration of an external defibrillator system connected to a patient in accordance with an exemplary embodiment of the invention.

FIG. 1 is a defibrillator system 20 that is configured to deliver a defibrillation shock to a patient 22, such as a victim of VF or cardiac arrest. The defibrillator system 20, includes, but is not limited to, an external defibrillator 24 having a connection part 26 that is configured to receive one or more electrodes (33,34). The external defibrillator 24 can be any number of external defibrillators, including, for example, an Automatic External Defibrillator or Automated External Defibrillator (AED), a semi-Automatic or semi-Automated External Defibrillator, or a manually operated external defibrillator. As used herein, an automatic or automated activity occurs without human intervention. While many of the exemplary embodiments of the invention apply to all types of external defibrillators, some of the embodiments are only for specific types, such as embodiments only for automated defibrillators or only for semi-automated defibrillators.

The external defibrillator 24 preferably includes a user interface 27 having a display 28 that is configured to visually present various measured or calculated parameters associated with the patient 22 and/or other information to a user (not shown) of the external defibrillator 24. For example, the display 28 can be configured to visually present the transthoracic impedance, ECG and/or other physiological signals of the patient 22, or instructions and/or commands, including CPR therapy instructions, to the user. The display 28 can also be configured to present visual alerts, flashing lights or warnings to the user. The user interface 27 can also include one or more input devices (e.g., switches or buttons) 30 that are configured to receive commands or information from the operator. The user interface 27 can also include an audio system that provides an audio signal to the user in the form of voice prompts that deliver instructions or commands, ascending, descending or quickening tones to indicate warnings, or any other suitable audio signals for communicating with the user. Additionally, the visual display 28 and audio signal may be configured to cooperate with one another.

The external defibrillator 24 is configured to generate a charge that is delivered to the patient 22 as the defibrillation shock with one or more electrodes (32, 34). The one or more electrodes (32, 34) may also be configured to sense one or more physiological and/or physical parameters of the patient 22 and supply signals representative of these parameters to the external defibrillator 24. As shown in phantom in FIG. 1, the defibrillator system may additionally include one or more sensing electrodes (36,38) to sense the physiological and/or physical parameters. In either configuration, the signals provided by the one or more electrodes (32,34) are preferably evaluated by the external defibrillator 24 to determine, among other things, whether a defibrillation shock should be applied to patient 22 in accordance with techniques known to those of ordinary skill in the art. This external defibrillator 24 can also evaluate the signals provided by the one or more electrodes (32,34) and/or one or more sensing electrodes (36,38) to determine the waveform parameters of the defibrillation shock such as the magnitude and duration of the shock.

Figure 2:
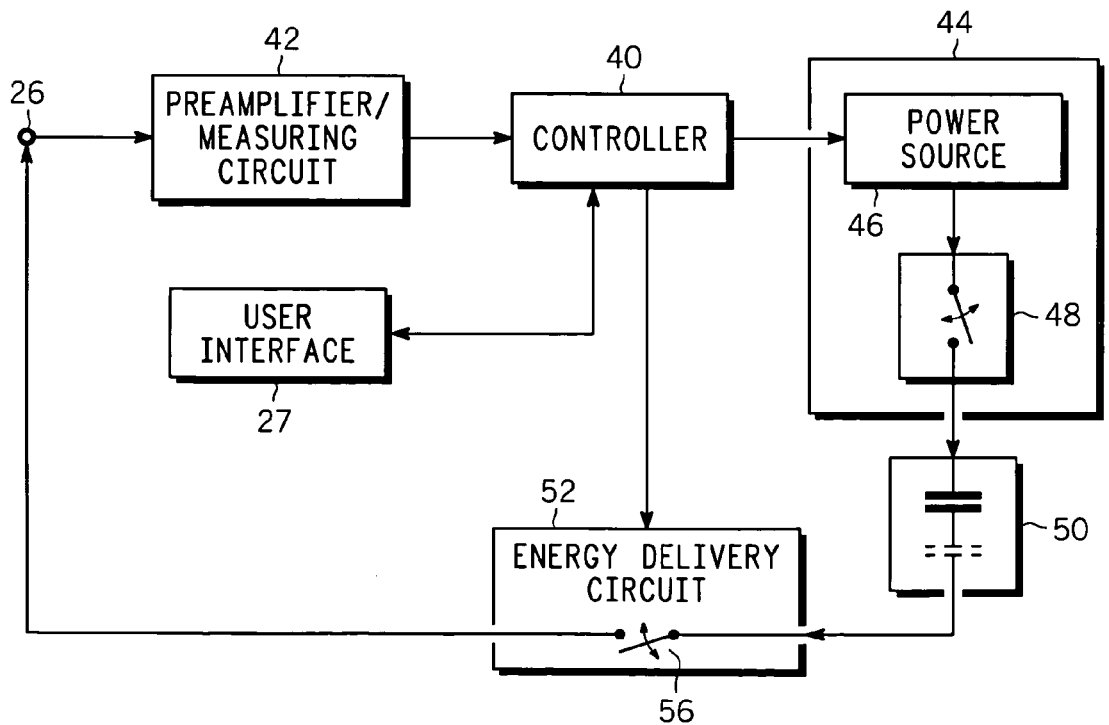
FIG. 2 is a simplified block diagram of an external defibrillator in accordance with a first exemplary embodiment of the invention.

Referring to FIG. 2, a simplified block diagram of the circuitry that makes up the external defibrillator 24 is illustrated in accordance with an exemplary embodiment. The external defibrillator 24 preferably includes a controller 40, the user interface 27 (e.g., switches or buttons 30 and/or display 28 as shown in FIG. 1), a pre-amplifier/measuring circuit 42, a charging mechanism 44 that can include a power source 46 and a switch 48. Switch 48 couples the power source 46 to one or more energy storage devices (e.g., capacitors) 50 and an energy delivery circuit 52, which is illustrated as a switch 56. Switch 56 is configured to selectively couple the one or more energy storage devices 50 to the connection port 26 under the control of the controller 40. The energy delivery circuit 52 can be implemented with any number of circuit configurations. For example, in a biphasic circuit, an H-bridge circuit can be used. The controller 40 can be single processing unit or multiple processing units and can be implemented with software, hardware, or a combination of hardware and software.

The controller 40 is configured to at least partially control the operation of the external defibrillator 24. Preferably, the controller 40 is configured to make treatment determinations based on the sensed physical parameters. For instance, the controller 40 can be configured to determine an appropriate amount of CPR therapy, such as the duration of CPR or the number of chest compressions, or determine an appropriate magnitude to which to charge the energy storage device 50. Additionally, the controller 40 controls the charging of the one or more energy storage devices 50. The one or more energy storage devices 50 are configured either to charge up at a certain rate as instructed by the controller 40, or charge up to a desired magnitude and maintain the charge once energized.

Figure 3:
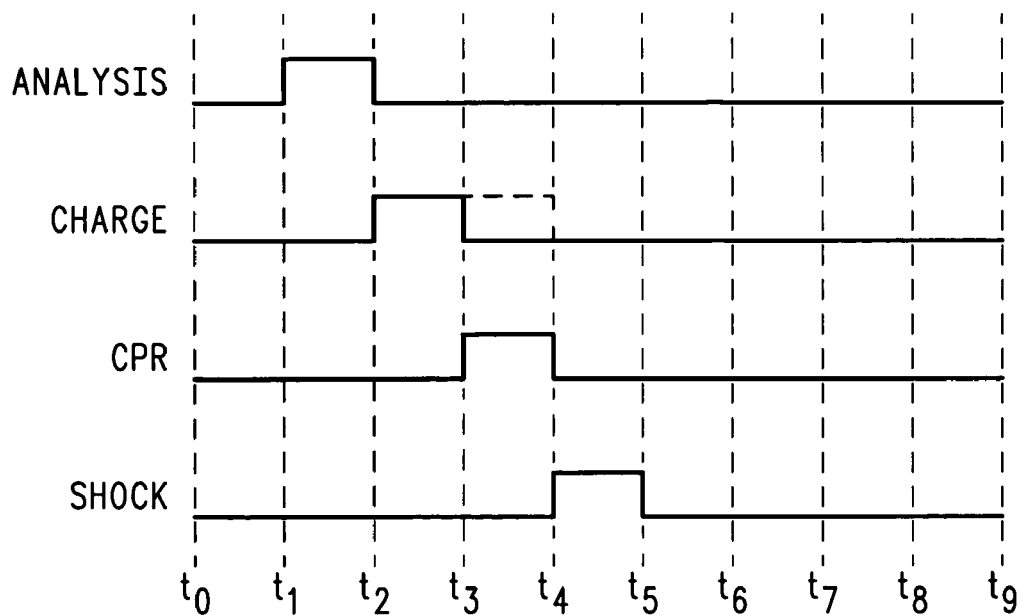
FIG. 3 is an exemplary timing diagram that shows the operational timing of the external defibrillator of FIG. 2 in accordance with a first exemplary embodiment of the invention.

Referring to FIG. 3, a timing diagram 54 is presented that illustrates the operational timing of the external defibrillator 24 in accordance with an exemplary embodiment of the invention. While successive events presented in the timing diagram are shown as beginning at the same time instant as preceding events end, it should be appreciated that delays can exist and the events do not need to begin and end at the same time instant as illustrated in FIGS. 3–6. Rather, one event can end before or after another time instance. Moreover, although the time intervals between the time instants appear to be substantially equal to each other, it should be further appreciated that the time intervals do not have to be equal and may vary. The time intervals shown in the timing diagrams are for illustration purposes only.

The external defibrillator 24 is activated at an initial time instant ($t_0$). This activation can be accomplished using any number of techniques such as activation of one of the input switches 30 shown in FIG. 1. After activation of the external defibrillator 24 at time instant ($t_0$), one or more physical parameters of the patient are sensed via the one or more electrodes (32,34,36,38) and analyzed to determine whether the patient should receive a defibrillation shock at time instant ($t_1$). It will be appreciated that any number of physical parameters can be sensed. For example, the sensed physical parameter can be ECG data, heart rhythm data, heart rate data, impedance data, blood pressure data, blood oxygen saturation data or any other physical parameter that is used in the art to assess the cardiac condition of a patient. A determination is made as to whether the patient has a heart rhythm to which a defibrillation shock can be applied, for example, whether the patient's ECG signal indicates a shockable rhythm. The signal or signals associated with the sensed physical parameters are preferably provided to the pre-amplifier/measuring circuit 42 for preprocessing and/or amplification. The controller 40 receives the signals from the pre-amplification circuit 42 and determines whether or not a shock should be delivered to the patient, by analyzing the sensed physical parameters. If the controller 40 determines that the patient should receive a shock, the controller 40 receives one or more charging parameters beginning at a second time instant ($t_2$). One of the charging parameters determined by the controller 40, which is at least partially based upon the physical parameter, is a charge for the one or more energy storage devices 50 that provides the desired defibrillation shock for the patient. This determination can be accomplished using any number of techniques known to those of ordinary skill in the art. The one or more energy storage devices 50 are charged at a suitable rate, including, but not limited to fixed or preset charging rates, computed charging rates, rates that can be adjusted prior to and/or during charging based upon any number of factors such as the results of a physiology analysis. In addition, the charging of the one or more energy storage devices 50 can be accomplished using any number of charging apparatuses (e.g., one or more charging circuits) that are preferably controlled by the controller 40.

Once the energy storage device 50 is charged to a charge magnitude, the charging ceases and the energy is stored within the energy storage device 50 beginning at about time instant ($t_3$) (shown in phantom). At about the same time instant ($t_3$), the controller 40 causes the user interface 27 to prompt the user to administer CPR to the patient. The controller 40 is preferably configured to provide verbal instructions or to display step by step commands for administering CPR therapy. The controller 40 is also preferably configured to prompt the user to deliver CPR for a predetermined time period, which may be a factory presetting or a preset by the user and which may be, for instance, between about 15 seconds and about 5 minutes, or for a predetermined number of chest compressions, for instance for about 100 chest compressions. The controller 40 can also be configured to determine the CPR therapy period or the amount of CPR therapy needed by the patient based upon the sensed physical parameters. For illustrative purposes, the completion of CPR delivery is shown to occur at about time instant ($t_4$). Consequently, the charge in the energy storage device 50 is maintained for a period of time that is at least sufficient to allow the user to deliver CPR therapy to the patient and until the defibrillation shock is ready to be administered to the patient (the delivery of the defibrillation shock is further discussed below). For example, if the predetermined time period to deliver CPR therapy to the patient is 5 minutes, then the energy storage device 50 charges and stores the charge for at least 5 minutes.

Prior to the delivery of the shock, it is preferable that the controller 40 prompts the user to end the CPR session and step away from the patient. The controller 40 can deploy an audible warning signal or a flashing light for an amount of time, preferably no longer than about 3 seconds, signifying to the user that the defibrillation shock is about to be deployed. Subsequently, preferably about 3 seconds after the beginning of the warning signal, the defibrillation shock is administered to the patient at about time instant ($t_4$) via the electrodes 32, 34. Alternatively, in the case of a semi-automatic defibrillator, it is preferable that the controller 40 prompts the user to end the CPR sessions, to step away from the patient, and to deliver the defibrillation shock. Recent research has shown that the less time that passes between the end of the CPR therapy and the delivery of a defibrillation shock the better chances a patient has of survival. Thus, it is most preferable that as little time as possible pass between the end of the CPR therapy and the delivery of a shock, more preferably to allow less than about 3 seconds to pass and preferable to allow less than about 10 seconds to pass.

Figure 4:
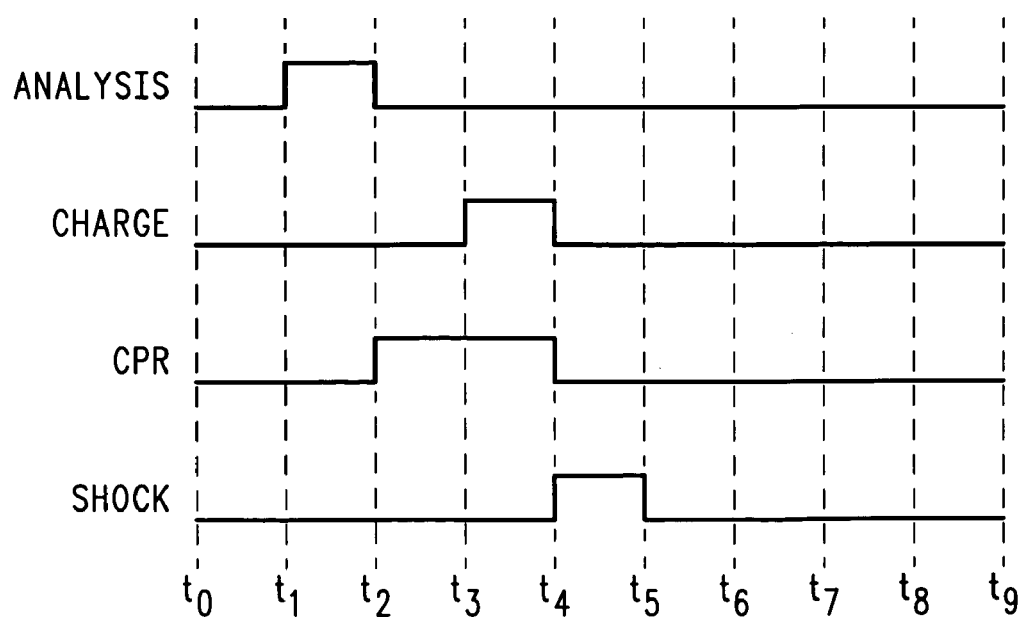
FIG. 4 is an exemplary timing diagram that shows the operational timing of the external defibrillator of FIG. 2 in accordance with a second exemplary embodiment of the invention.

Turning to FIG. 4, timing diagram 55 illustrates the operational timing of the external defibrillator in accordance with an alternative exemplary embodiment. In this embodiment, CPR therapy is administered before the one or more storage devices 50 are charged. Thus, after activation of the external defibrillator 24 at time instant ($t_0$), one of more physical parameters of the patient are sensed via the one or more electrodes (32,34,36,38) and analyzed at time instant ($t_1$). Similar to the previous embodiment, the controller 40 determines whether the patient has a heart rhythm to which a defibrillation shock can be applied, for example, whether the patient's ECG signal indicates a shockable rhythm and, if so the controller 40 causes the user interface 27 to prompt the user to administer CPR therapy to the patient for a predetermined period at time instant ($t_2$). As previously discussed, the predetermined period can be a predetermined duration of time that is a factory or user preset or determined by the controller 40. Alternatively, the predetermined amount can be a predetermined number of chest compressions. Then, at a time instant during the predetermined CPR therapy period, shown in FIG. 4 as time instant ($t_3$), the controller 40 receives one or more charging parameters beginning some time during the administration of CPR therapy and charges one or more of the energy storage devices 50 for preparation of the delivery of a defibrillation shock to the patient. Prior to the delivery of the shock, it is preferable that the controller 40 prompts the user to end the CPR session and step away from the patient. Subsequently, the defibrillation shock is administered to the patient at about time instant ($t_4$) via the electrodes 32,34.

Figure 5:
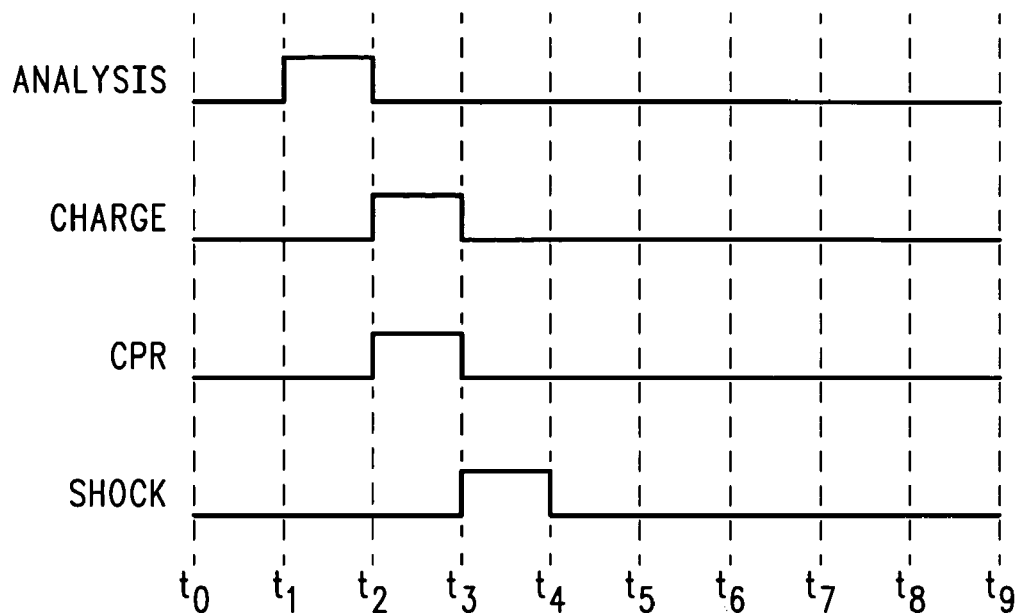
FIG. 5 is an exemplary timing diagram that shows the operational timing of the external defibrillator of FIG. 2 in accordance with a third exemplary embodiment of the invention.

In another embodiment, shown in FIG. 5, timing diagram 56 illustrates the operational timing of the external defibrillator in accordance with an alternative exemplary embodiment. With this embodiment, after the controller 40 determines that the patient has a shockable rhythm, based on the analysis of the sensed physical parameters, and begins to charge the energy storage device, the controller 40, at about the same time instant ($t_2$), causes the user interface 27 to prompt the user to administer a desired amount of CPR. The controller 40 also begins charging the energy storage device 50 to a suitable charge magnitude and at a suitable rate, so that CPR can be administered while energy storage device 50 charges. Thus, the controller 40 preferably determines a charging rate to substantially achieve the determined charge magnitude at about the same time that a desired period of CPR therapy is completed, which is illustrated as occurring at about time instant ($t_3$). The charging rate can be determined using any number of techniques. For example the charging rate ($Q_{Rate}$) can be determined as follows:

$$Q_{Rate}=(Q_{Initial}-Q_{final})/Time_{CPR} \quad (1)$$

Where $Q_{Initial}$ is magnitude of the initial charge when charging begins, $Q_{final}$ is magnitude of the final charge (i.e., the charge for the one or more energy storage devices 50 that provides the desired defibrillation shock for the patient) and $Time_{CPR}$ is the time it takes to complete delivery of a desired period of CPR therapy, which can be the minimum time, maximum time, or average time to complete the delivery of a desired period of CPR therapy. The minimum time, maximum time or average time will vary depending upon, for example, the measurement scheme and physiological analysis conducted by the controller 40.

After the energy storage device 50 reaches the desired charge magnitude, the controller 40 causes the user interface 27 to indicate to the user that the defibrillator is fully charged. As before, the controller 40 preferably deploys an audible sound, such as an ascending tone or a quickening tap, or any other means of communicating with a user. At about the same time, the interface 27 indicates to the user, either visually or audibly, to back away from the patient so that the defibrillation shock can be delivered soon after to the patient or the user can be prompted to administer the shock soon after. At about time instant ($t_3$), the defibrillator then delivers the defibrillation shock. Alternatively, the defibrillator can be configured to prompt the user to deliver the shock.

Figure 6:
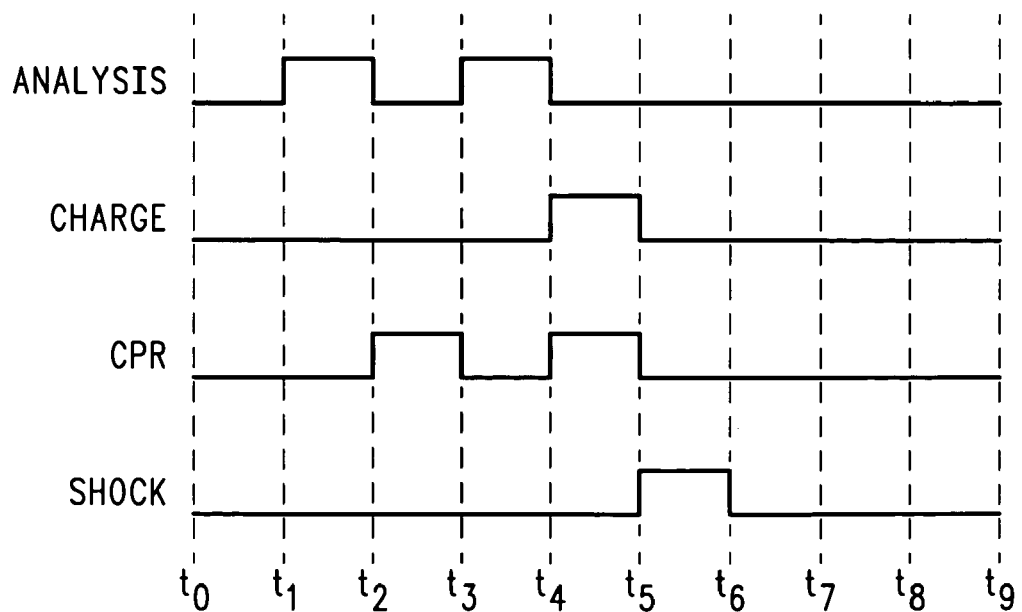
FIG. 6 is an exemplary timing diagram that shows the operational timing of the external defibrillator of FIG. 2 in accordance with a fourth exemplary embodiment of the invention.

In FIG. 6, the timing diagram 58 depicts yet another example for the operation of the defibrillator. In this embodiment, once the controller 40 has determined that a patient's physical parameters, i.e. ECG signal, indicates a shockable rhythm, the controller 40 calculates a viability index from the sensed physical parameters to determine whether applying a defibrillation shock to a patient will yield a favorable response and whether defibrillation should be initially initiated or whether CPR therapy should first be administered to increase heart viability. The duration of CPR therapy can also be determined by analyzing the viability index, and specifically, can be varied coarsely or finely based upon the analysis results. The viability index can be determined in numerous ways including evaluating the amplitude of the ECG signal, or determining the centroid or median frequency of the heart rhythm. Other ways to determine the viability index are disclosed in U.S. Patent Application Publication No. 2002/0161407 A1, incorporated herein by reference. Once the viability index is determined, it is compared against a predetermined numerical threshold that defines the minimum threshold of viability for a heart depending on the factors used to measure viability. To determine the duration of CPR therapy, the viability index is compared against multiple predetermined thresholds to determine a recommended length of CPR therapy or a recommended number of CPR compressions.

Turning back to FIG. 6, after activation of the external defibrillator 24 at the initial time instant ($t_0$), one or more physical parameters of the patient, such as ECG data, are sensed with the one or more of the electrodes (32,34,36,38) at time instant ($t_1$). The controller 40 is configured to calculate the viability index from the sensed physical parameters and, based on the viability index, to determine whether or not a patient's heart has high or low viability. This determination may be achieved in any one of numerous ways such as, for example, comparing the viability index to predetermined threshold values. If the controller 40 determines that the viability index is above the predetermined threshold, thereby indicating low heart viability, the controller 40 prompts the user to administer a predetermined amount of CPR during a predetermine period of time instant ($t_2$) and does not initiate charging of the energy storage device 50. If the controller 40 determines that the viability index is below the predetermined threshold, high heart viability is indicated and the controller 40 begins to charge the defibrillator (not illustrated in FIG. 6).

As a further example, the controller 40 can be configured to extract the scaling exponent from ECG data collected from the patient to determine whether the scaling exponent is greater than a given threshold. As known in the art, as the scaling exponent increases, the viability of the heart decreases. Generally, administration of CPR therapy can decrease the scaling exponent and increase heart viability. Thus, if the controller 40 determines that the scaling exponent is high, indicating low heart viability, a signal is sent to the user interface 27 to prompt the user to administer CPR at time instant ($t_2$) and the controller 40 does not initiate charging of the energy storage device 50. After administration of CPR therapy, more ECG data is obtained and analyzing at time instant ($t_3$) to evaluate whether the scaling exponent has decreased. If the scaling exponent increases or stays the same, the controller 40 will again indicate to the user that more CPR must be administered and prompts the user to administer the CPR therapy for a predetermined amount of time or compression (not illustrated in FIG. 6). The administration of CPR therapy and the subsequent collection and analysis of ECG data can be repeated as many times as necessary until the heart rhythm indicates a scaling exponent that is lower than the predetermined threshold, or alternatively, a higher heart viability.

If the scaling exponent is initially found to be low, indicating high heart viability, controller 40 then determines one or more charging parameters and causes the energy storage device 50 to charge at time instant ($t_4$). At substantially the same time ($t_4$), the controller 40 also causes the user interface 27 to prompt the user to administer CPR therapy for a predetermined period. The energy storage device 50 is charged at a rate, and for an amount of time, sufficient for the user to deliver the predetermined period of CPR therapy. Alternatively, the energy storage device 50 is charged to a desired charge magnitude and maintains the charge until the desired CPR therapy period is delivered. Soon after the CPR therapy delivery and after the energy storage device 50 is fully charged, the defibrillator either prompts the user to deliver the shock to the patient at time instant ($t_5$) or automatically delivers the shock to the patient.

The methods and apparatuses disclosed herein greatly improve the timing between the delivery of CPR therapy and the administration of a defibrillation shock to a patient. The invention accomplishes this by providing an external defibrillator and a method by which to use the external defibrillator that does not compromise the safety of the user or the patient. Additionally, the invention does not greatly increase the cost or size of a defibrillator. The disclosed inventions may be implemented in all types of external defibrillators, including fully automatic, semi-automatic, fully automated or semi-automated and manual defibrillators.

While a finite number of exemplary embodiments have been presented in the foregoing detailed description of the invention, it should be appreciated that a vast number of variations exist. It should also be appreciated that the exemplary embodiments are only examples, and are not intended to limit the scope, applicability, or configuration of the invention in any way. Rather, the foregoing detailed description will provide those skilled in the art with a convenient road map for implementing exemplary embodiments of the invention. It being understood that various changes may be made in the function and arrangement of elements described in an exemplary embodiment without departing from the scope of the invention as set forth in the appended claims.

What is claimed is:

1. A method of controlling an external defibrillator configured to supply a defibrillation shock to a patient, comprising the steps of:
   obtaining and analyzing a physical parameter from the patient, while CPR therapy is not being administered, to determine whether the patient should be treated with a defibrillation shock;
   obtaining a viability index from the physical parameter and comparing the viability index to a predetermined threshold to identify whether a heart condition treatable initially with a defibrillation shock is indicated or whether a heart condition treatable initially with CPR therapy is indicated and comparing the viability index to a predetermined CPR therapy threshold to determine a recommended CPR therapy period;
   indicating that CPR therapy should be administered for the recommended CPR therapy period, and charging an energy storage device for at least a portion of the predetermined CPR therapy period; and
   discharging the energy storage device to thereby supply the defibrillation shock to the patient, after the predetermined CPR therapy period.

2. The method of claim 1, wherein the CPR therapy period is a duration of time.

3. The method of claim 1, wherein the CPR therapy period is a number of chest compressions.

4. The method of claim 1, wherein the step of indicating further comprises:
   charging the energy storage device to a charge magnitude at a predetermined charge rate.

5. The method of claim 4, wherein the predetermined charge rate is a value such that the energy storage device is charged to the charge magnitude in a time that is substantially equivalent to the recommended CPR therapy period.

6. The method of claim 1, wherein the step of indicating further comprises charging the energy storage device to a charge magnitude and maintaining the charge magnitude, for the predetermined CPR therapy period.

7. The method of claim 1, wherein the step of indicating further comprises visually indicating that CPR therapy should be administered for the recommended CPR therapy period.

8. The method of claim 1, wherein the step of indicating further comprises audibly indicating the CPR therapy should be administered for the recommended CPR therapy period.

9. The method of claim 1, wherein the step of discharging further comprises discharging the energy storage device less than ten seconds after the recommended CPR therapy period.

10. The method of claim 1, wherein the recommended CPR therapy period is a measure of time.

11. The method of claim 1, wherein the recommended CPR therapy period is a number of chest compressions.

12. A method comprising the steps of:
    obtaining and analyzing a physical parameter from the patient, while CPR therapy is not being administered, to determine whether the patient should be treated with a defibrillation shock;
    charging an energy storage device to a charge magnitude, if the patient should be treated with a defibrillation shock;
    obtaining a viability index from the physical parameter;
    comparing the viability index to a predetermined threshold to identify whether a heart condition treatable initially with a defibrillation shock is indicated or whether a heart condition treatable initially with CPR therapy is indicated and comparing the viability index to a predetermined CPR therapy threshold to determine a recommended CPR therapy period;
    indicating that CPR therapy should be administered for the recommended CPR therapy period and maintaining the charge magnitude for at least a portion of the recommended CPR therapy period; and
    discharging the energy storage device to thereby supply the defibrillation shock to the patient, after the predetermined CPR therapy period.

13. The method of claim 12, wherein the CPR therapy period is a duration of time.

14. The method of claim 12, wherein the CPR therapy period is a number of chest compressions.

15. The method of claim 12, wherein the step of charging the energy storage device comprises:
    charging the energy storage device to a predetermined charge rate.

16. The method of claim 15, wherein the predetermined charge rate is a value such that the energy storage device is charged to the charge magnitude in a time that is substantially equivalent to the predetermined CPR therapy period.

17. The method of claim 12, wherein the step of indicating further comprises visually indicating that CPR therapy should be administered for the predetermined CPR therapy period.

18. The method of claim 12, wherein the step of indicating further comprises audibly indicating that CPR therapy should be administered for the predetermined CPR therapy period.

* * * * *